United States Patent
Torniainen et al.

(10) Patent No.: US 11,686,327 B2
(45) Date of Patent: Jun. 27, 2023

(54) INERTIAL PUMPS

(71) Applicant: Hewlett-Packard Development Company, L.P., Spring, TX (US)

(72) Inventors: Erik D. Torniainen, Corvallis, OR (US); Alexander Govyadinov, Corvallis, OR (US); Pavel Kornilovich, Corvallis, OR (US); David P. Markel, Corvallis, OR (US)

(73) Assignee: Hewlett-Packard Development Company, L.P., Spring, TX (US)

(*) Notice: Subject to any disclaimer, the term of this patent is extended or adjusted under 35 U.S.C. 154(b) by 958 days.

(21) Appl. No.: 16/493,344

(22) PCT Filed: Apr. 7, 2017

(86) PCT No.: PCT/US2017/026562
§ 371 (c)(1),
(2) Date: Sep. 12, 2019

(87) PCT Pub. No.: WO2018/186881
PCT Pub. Date: Oct. 11, 2018

(65) Prior Publication Data
US 2021/0010488 A1    Jan. 14, 2021

(51) Int. Cl.
*F04F 7/00* (2006.01)
*B01L 3/00* (2006.01)
(Continued)

(52) U.S. Cl.
CPC ............ *F04F 7/00* (2013.01); *B01L 3/50273* (2013.01); *B01L 3/502738* (2013.01);
(Continued)

(58) Field of Classification Search
CPC .. F04F 7/00; B01L 3/50273; B01L 3/502738; B01L 2200/16; B01L 2400/0605; B81B 1/006; B81B 2201/051; B81B 2203/0338
(Continued)

(56) References Cited

U.S. PATENT DOCUMENTS 5,331,928 A * 7/1994 Wood ................ F02B 75/044
123/78 B
6,620,273 B2   9/2003 Dai et al.
(Continued)

FOREIGN PATENT DOCUMENTS

CN        105940249 A     9/2016
JP         2015211965      11/2015
(Continued)

OTHER PUBLICATIONS

Rahal et al., Symmetrical Bail Check-Valve Based Rotation-Sensitive Pump, Journal of Fluids Engineering, vol. 135, Nov. 2013, 9 pages.
(Continued)

*Primary Examiner* — Christine T Mui
(74) *Attorney, Agent, or Firm* — Foley & Lardner LLP (57) ABSTRACT

The present disclosure is drawn to inertial pumps. An inertial pump can include a microfluidic channel, a fluid actuator located in the microfluidic channel, and a check valve located in the microfluidic channel. The check valve can include a moveable valve element, a narrowed channel segment located upstream of the moveable valve element, and a blocking element formed in the microfluidic channel downstream of the moveable valve element. The narrowed channel segment can have a width less than a width of the moveable valve element so that the moveable valve element can block fluid flow through the check valve when the moveable valve element is positioned in the narrowed
(Continued)

channel segment. The blocking element can be configured such that the blocking element constrains the moveable valve element within the check valve while also allowing fluid flow when the moveable valve element is positioned against the blocking element.

15 Claims, 10 Drawing Sheets

(51) Int. Cl.
    *B81B 1/00* (2006.01)
    *F04B 53/10* (2006.01)

(52) U.S. Cl.
    CPC .............. *B81B 1/006* (2013.01); *F04B 53/10* (2013.01); *B01L 2200/141* (2013.01); *B01L 2200/16* (2013.01); *B01L 2400/0605* (2013.01); *B81B 2201/051* (2013.01); *B81B 2203/0338* (2013.01)

(58) Field of Classification Search
    USPC ........................................................ 417/240
    See application file for complete search history.

(56) References Cited

U.S. PATENT DOCUMENTS

| | | |
|---|---|---|
| 7,290,554 B2 | 11/2007 | Koeneman et al. |
| 7,942,160 B2 | 5/2011 | Jeon et al. |
| 8,096,786 B2 | 1/2012 | Bullock |
| 9,056,291 B2 | 6/2015 | Battrell et al. |
| 9,395,050 B2 | 6/2016 | Kornilovich et al. |
| 2008/0277005 A1 | 11/2008 | Unger et al. |
| 2013/0061962 A1 | 3/2013 | Kornilovich et al. |
| 2013/0063528 A1* | 3/2013 | Govyadinov .......... B41J 2/1404 347/68 |
| 2014/0377145 A1 | 12/2014 | Govyadinov et al. |
| 2015/0093815 A1 | 4/2015 | Kiani et al. |
| 2016/0114319 A1 | 4/2016 | McGinness et al. |
| 2016/0220997 A1 | 8/2016 | Mescher et al. |
| 2016/0341337 A1 | 11/2016 | Govyadinov et al. |

FOREIGN PATENT DOCUMENTS

| | | |
|---|---|---|
| WO | 2014046687 | 3/2014 |
| WO | 2016/024998 A1 | 2/2016 |
| WO | 2016/120252 A1 | 8/2016 |
| WO | 2016122554 | 8/2016 |
| WO | 2016122635 | 8/2016 |
| WO | 2016122706 | 8/2016 |
| WO | 2017047032 | 3/2017 |

OTHER PUBLICATIONS

International Search Report dated Dec. 28, 2017 for PCT/US2017/026562, Applicant Hewlett-Packard Development Company, L.P.

* cited by examiner

INERTIAL PUMPS

BACKGROUND

Microfluidics relates to the behavior, precise control and manipulation of fluids that are geometrically constrained to a small, typically from sub-millimeter down to several micrometers, scale. Numerous applications can benefit from fluid flow control techniques, such as pumping, valves, and so on. Due to the small size of microfluidic systems, these components can be difficult to design and often involve trade-offs in complexity, size, cost, and effectiveness.

BRIEF DESCRIPTION OF THE DRAWINGS

Additional features and advantages of the disclosure will be apparent from the detailed description which follows, taken in conjunction with the accompanying drawings, which together illustrate, by way of example, features of the present technology.

Reference will now be made to several examples that are illustrated herein, and specific language will be used herein to describe the same. It will nevertheless be understood that no limitation of the scope of the disclosure is thereby intended.

DETAILED DESCRIPTION

The present disclosure is drawn to inertial pumps and microfluidic devices including inertial pumps. In one example, an inertial pump can include a microfluidic channel, a fluid actuator located in the microfluidic channel, and a check valve located in the microfluidic channel. The check valve can include a moveable valve element, a narrowed channel segment located upstream of the moveable valve element, and a blocking element formed in the microfluidic channel downstream of the moveable valve element. The narrowed channel segment can have a width that is less than a width of the moveable valve element so that the moveable valve element blocks fluid flow through the check valve when the moveable valve element is positioned in the narrowed channel segment. The blocking element can be configured such that the blocking element constrains the moveable valve element within the check valve while also allowing fluid flow when the moveable valve element is positioned against the blocking element.

In certain examples, the fluid actuator can be a resistor configured to generate vapor bubbles to displace fluid in the microfluidic channel. In a particular example, the microfluidic channel and the check valve can be fabricated by photolithography. In some cases, the moveable valve element can have the form of a cylinder or a hexagonal block.

In further examples, a distance between the blocking element and the narrowed channel segment can be from 1.1 to 5 times the width of the moveable valve element. In still further examples, the inertial pump can include gaps between the moveable valve element and the ceiling and floor of the microfluidic channel. The gaps can have a height from about 0.05 µm to about 4 µm. In another example, the check valve can be located from 1 µm to 10 µm away from the fluid actuator.

In certain examples, the check valve can be located downstream of the fluid actuator. In particular example, the inertial pump can also include a second check valve located upstream of the fluid actuator.

The present disclosure can also extend to microfluidic devices incorporating inertial pumps. In one example, a microfluidic device can include a fluid reservoir, a microfluidic channel in communication with the fluid reservoir, a fluid actuator located in the microfluidic channel, and a check valve located in the microfluidic channel. The check valve can include a moveable valve element, a narrowed channel segment located upstream of the moveable valve element, and a blocking element formed in the microfluidic channel downstream of the moveable valve element. The narrowed channel segment can have a width that is less than a width of the moveable valve element so that the moveable valve element blocks fluid flow through the check valve when the moveable valve element is positioned in the narrowed channel segment. The blocking element can be configured such that the blocking element constrains the moveable valve element within the check valve while also allowing fluid flow when the moveable valve element is positioned against the blocking element.

In certain examples, the check valve can be configured to allow fluid flow away from the fluid reservoir. In a further example, the microfluidic device can also include a second fluid reservoir in communication with the microfluidic channel. The check valve can be located along the microfluidic channel between the first fluid reservoir and the second fluid reservoir. The second fluid reservoir can have a higher or lower pressure than the first fluid reservoir.

In another example, a microfluidic device can include a microfluidic mixing channel, a first fluid reservoir, a first inertial pump fluidly connected between the first fluid reservoir and the microfluidic mixing channel to pump a first fluid from the first fluid reservoir into the microfluidic mixing channel, a second fluid reservoir, and a second inertial pump fluidly connected between the second fluid reservoir and the microfluidic mixing channel to pump a second fluid from the second fluid reservoir into the microfluidic mixing channel. One or both of the first and second inertial pumps can include a microfluidic channel, a fluid actuator located in the microfluidic channel, and a check valve located in the microfluidic channel. The check valve can include a moveable valve element, a narrowed channel segment located upstream of the moveable valve element, and a blocking element formed in the microfluidic channel downstream of the moveable valve element. The narrowed channel segment can have a width that is less than a width of the moveable valve element so that the moveable valve element blocks fluid flow through the check valve when the moveable valve element is positioned in the narrowed channel segment. The blocking element can be configured such that the blocking element constrains the moveable valve element within the check valve while also allowing fluid flow when the moveable valve element is positioned against the blocking element.

In certain examples, the microfluidic device can also include one or more additional first inertial pumps fluidly connected between the first fluid reservoir and the microfluidic channel, and one or more additional second inertial pumps fluidly connected between the second fluid reservoir and the microfluidic mixing channel. In a further example, the microfluidic mixing channel can lead to a reactor.

Many microfluidic applications involve control of fluid flow through small microfluidic channels. These channels can often have widths of less than 100 μm, for example. Accordingly, components used for controlling fluid flow in microfluidic channels are often very small in size. Constructing pumps and valves at this scale can be challenging. Some examples of previous solutions include dynamic valves, wax valves, capillary break valves, microelectromechanical (MEMS) valves, piezoelectric valves. These solutions have various drawbacks, such as high cost, complexity, inability to use the valves more than once, low effectiveness of the valves, inability to work against a pressure head, and slow response times.

Additionally, inertial pumps have been devised that use a fluid actuator such as a resistor or a piezoelectric element to displace fluid in a microchannel. The fluid actuator can be at a point along the microchannel that is asymmetric with respect to the length of the microchannel. When the fluid actuator repeatedly displaces fluid, such as by repeatedly forming a vapor bubble in the fluid or actuating a piezoelectric element, a net flow of fluid in one direction can be achieved due to inertial forces of the fluid in the microchannel moving in to replace the fluid displaced by the bubble or the piezoelectric element. Such inertial pumps can create fluid flow in microfluidic systems. However, a disadvantage of these pumps is the inability to work against a significant pressure head.

Accordingly, the present disclosure provides inertial pumps with integrated check valves. The check valves can reduce or substantially prevent backflow of fluid toward the fluid actuator of the inertial pump, even against significant pressure heads. The check valves can also be manufactured easily using the same techniques used to form the microfluidic channels themselves. Additionally, the check valves can respond, i.e., open and close in response to change in fluid flow direction, with a response time on the order of several microseconds. Thus, the inertial pumps with integrated check valves described herein can solve many of problems previously faced in the area of controlling microfluidic flow. In some applications, the inertial pumps described herein can be used to pump different fluids from multiple reservoirs into a single channel or reactor while the check valves can prevent cross contamination due to a fluid from one reservoir entering other reservoirs. In a particular example, this can be useful in certain biological testing such as DNA testing, where the tests can benefit from reactants being kept separate and uncontaminated before being pumped into a reactor.

Figure 1A:
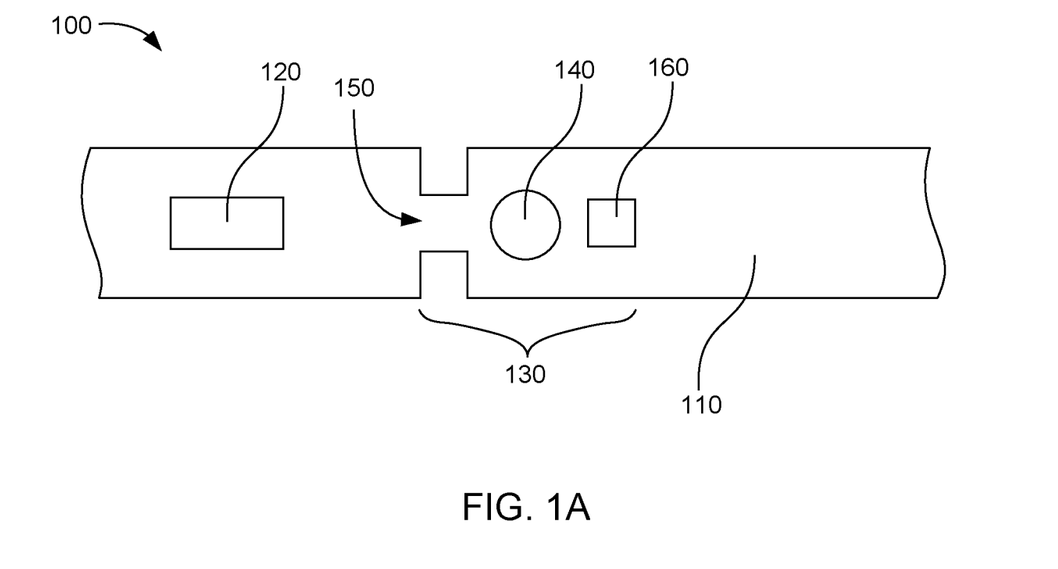
FIG. 1A is a top down schematic view of an example inertial pump in accordance with the present disclosure.
Figure 1B:
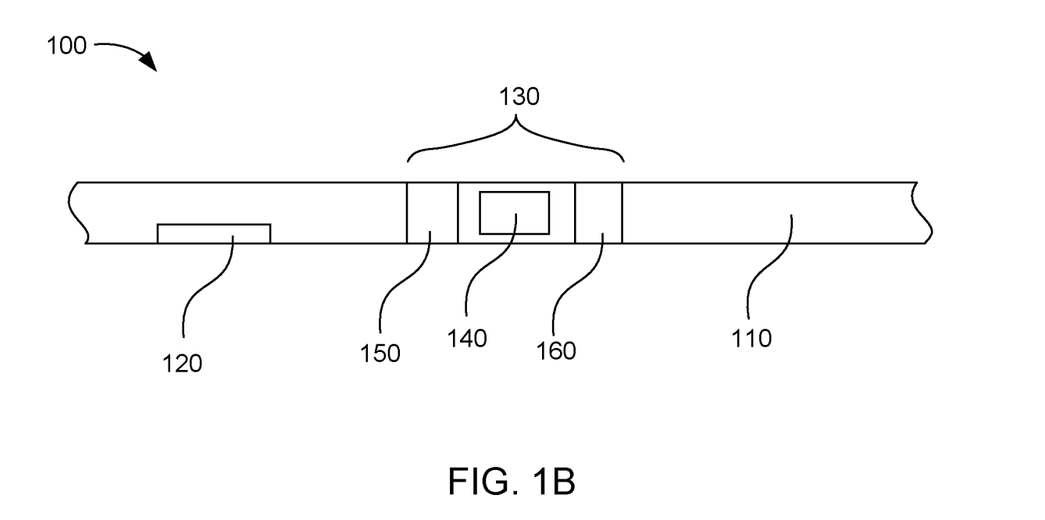
FIG. 1B is a side schematic view of an example inertial pump in accordance with the present disclosure with an open check valve.

FIGS. 1A-1D show an example of an inertial pump 100 according to the present technology. FIG. 1A shows a top down schematic view of the inertial pump, which includes a microfluidic channel 110, a fluid actuator 120 located in the microfluidic channel, and a check valve 130 located in the microfluidic channel. The check valve includes a moveable valve element 140, a narrowed channel segment 150, and a blocking element 160. As used herein, "check valve" refers to the structures designated as reference numeral 130 (in other FIGS., 230, 330, 430, etc.) from the narrowed channel segment to the blocking element. In other FIGS., the check valve is numbers similarly FIG. 1B shows a side schematic view of the inertial pump 100. As shown in this figure, the fluid actuator can be formed as a pad on the floor of the microfluidic channel. In certain examples, the fluid actuator can be a thermal resistor or a piezoelectric element. The narrowed channel segment 150 can be formed as an integral part of the walls of the microfluidic channel. In this example the narrowed channel segment is formed as square-shaped protrusions extending inward from the walls of the microfluidic channel. The moveable valve element 140 can be disconnected from the floor and ceiling of the microfluidic channel, as shown in FIG. 1B. Thus, the moveable valve element can be free to move with the flow of fluid in the check valve. In this example, the blocking element 160 is formed as a square-shaped pillar that extends from the ceiling to the floor of the microfluidic channel. In other examples, the blocking element can be formed in a different shape that will effectively restrain the moveable valve element in the check valve while also allowing fluid flow to pass by. The blocking element can be fixed in place so that the blocking element does not move with the fluid flow.

Figure 1C:
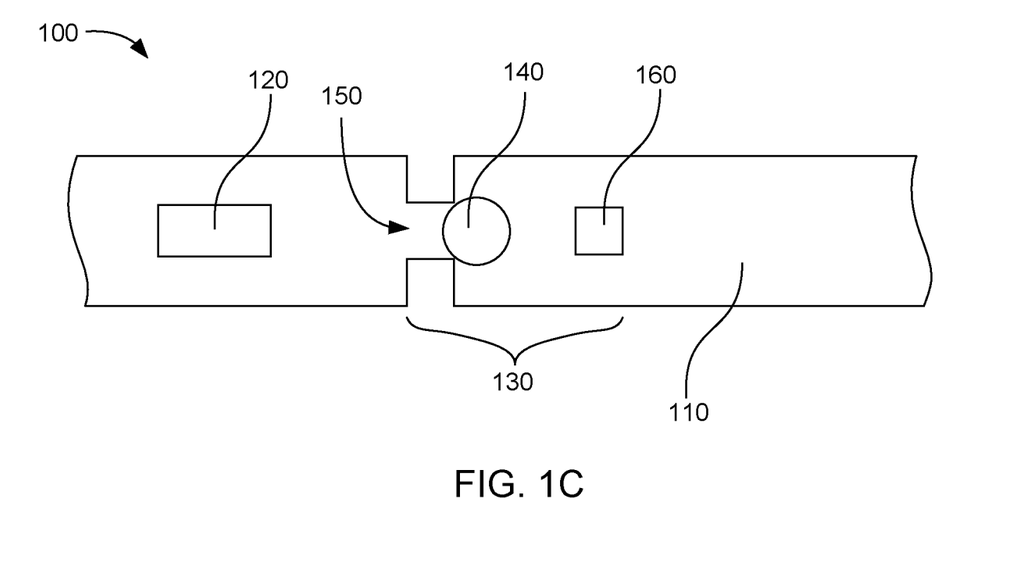
FIG. 1C is a top down schematic view of an example inertial pump in accordance with the present disclosure with a closed check valve.

FIG. 1C shows a top down schematic view of the inertial pump 100 when the check valve 130 is in a closed position. The moveable valve element 140 is positioned in the gap formed by the narrowed channel segment. The moveable valve substantially blocks or mostly blocks the narrowed channel segment so that fluid flow through the narrowed channel segment is substantially stopped or reduced. Depending on the height of the moveable valve element and gaps above and below the moveable valve element, a small amount of fluid flow can still occur above and below the moveable valve element. The check valve can be in this position when, for example, the fluid actuator 120 is not active and a higher pressure is present in the microfluidic channel downstream of the check valve. Thus, the check valve can prevent or reduce backflow through the inertial pump due to a pressure head downstream.

Figure 1D:
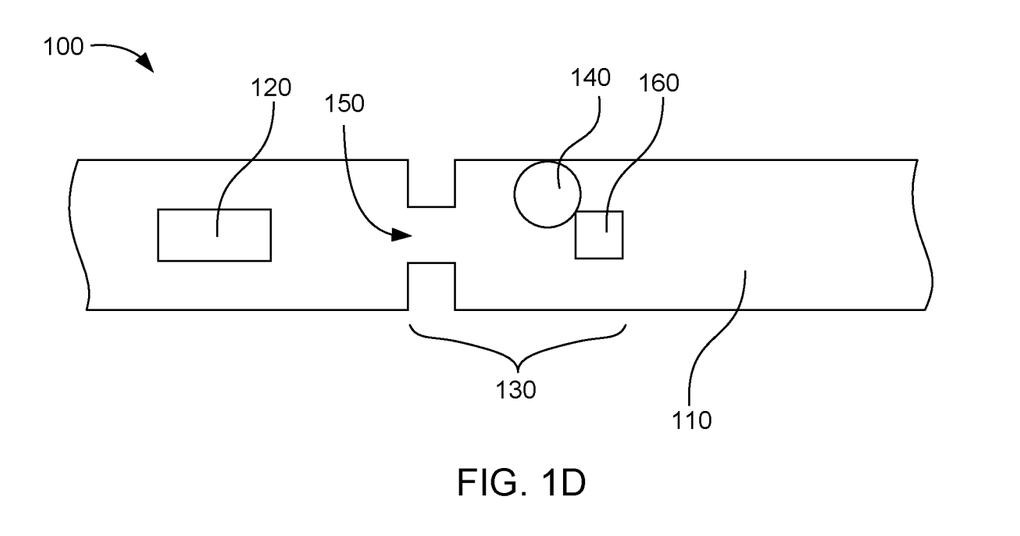
FIG. 1D is a top down schematic view of an example inertial pump in accordance with the present disclosure with an open check valve.

FIG. 1D shows a top down schematic view of the inertial pump 100 in an open position. The moveable valve element 140 is positioned against the blocking element 160. The blocking element is configured so that the blocking element can restrain the moveable valve element in the check valve 130 while still allowing fluid flow through. Specifically, in this example the blocking element is placed in the center of the microfluidic channel and sized so that the gap between the blocking element and the walls of the microfluidic channel is too small for the moveable valve element to pass through. When the fluid flows in the downstream direction, the moveable valve element moves with the flow and becomes lodged on one side of the blocking element. The gap on the other side of the blocking element is open to allow fluid to flow through.

In certain examples, the fluid actuator of the inertial pump can be a resistor configured to generate vapor bubbles to displace fluid in the microfluidic channel. Specifically, the resistor can be powered to quickly heat the fluid over the resistor past the boiling point of the fluid. This can produce a bubble that expands to force surrounding fluid in the microchannel away from the resistor. While the surrounding fluid is being forced away from the resistor, the check valve can be in an open position to allow fluid to flow past in the downstream direction. The bubble can then collapse. When the bubble collapses, surrounding fluid can rush back in to fill the volume that was occupied by the bubble. At this point, the fluid downstream of the resistor can tend to move back toward the resistor. However, the moveable valve element can move with the fluid moving back and quickly close the valve so that the fluid downstream of the valve is blocked from flowing back through. The remaining volume occupied by the collapsed bubble is then filled by drawing more fluid from upstream of the resistor. In this way, the net flow rate in the downstream direction produced by the inertial pump can be increased.

In other examples, the fluid actuator can be a piezoelectric element. These examples can work similarly to the examples including thermal resistors, except that instead of a resistor forming a bubble to displace fluid, a current can be applied to the piezoelectric element to cause the piezoelectric element to change shape and displace fluid in the microfluidic channel. When the current to the piezoelectric element is turned off, the piezoelectric element can return to its original shape. Fluid from upstream of the piezoelectric element can fill the volume that was occupied by the piezoelectric element, and the check valve can close to prevent fluid downstream from flowing back toward the piezoelectric element.

As used herein, "downstream" normally refers to the direction of fluid flow that an inertial pump is configured to generate when the inertial pump is active. In some examples, the check valve can be located downstream of the fluid actuator. When the inertial pump is active, the fluid actuator can repeatedly fire, moving fluid downstream, and the check valve can repeatedly open to allow downstream fluid flow while the fluid actuator is firing and then close to prevent backflow between firings of the fluid actuator. In alternative examples, the fluid actuator can be located downstream of the check valve. In this case, the check valve can close when the fluid actuator fires, prevent the fluid actuator from displacing fluid back through the check valve. Between firings of the fluid actuator, the check valve can open to allow fluid to flow in the downstream direction to replace the fluid displaced by the fluid actuator. As used herein, "upstream" refers to the direction opposite of downstream. Fluid flow in the upstream direction is typically prevented or slowed by the check valve.

In some examples, the shape and dimensions of the moveable valve element, narrowed channel segment, and blocking element can be chosen to allow the check valve to allow for a high fluid flow rate in the downstream direction, substantially block or reduce fluid flow in the upstream direction, and provide a fast response time. In certain examples, the spacing between the blocking element and the narrowed channel segment in the check valve can affect the fluid flow rate in the downstream direction and the response time of the check valve. A smaller spacing can reduce the response time of the check valve, while a larger spacing can increase the space available for fluid to flow through the check valve and thereby increase downstream fluid flow rate. In one example, the distance between the blocking element and the narrowed channel segment can be from 1.1 to 5 times the width of the moveable valve element. In further examples, the distance between the blocking element and the narrowed channel segment can be from about 1 µm to about 500 µm.

In many examples, the moveable valve element can be shaped as a cylinder. In such examples, the "width" of the moveable valve element can refer to the diameter of the cylinder. In other examples, the "width" of the moveable valve element can refer to the shortest dimension across the moveable valve element, i.e., orthogonal to the height of the moveable valve element. In certain examples, the moveable valve element can be shaped as a hexagonal block. The width of such a moveable valve element can be the distance between opposite parallel sides of the hexagon. In further examples, the moveable valve element can have square, rectangular, triangular, or a variety of other shapes. In each example, the width can be the shortest dimension across the moveable valve element. Thus, using a narrowed channel segment with a width smaller than the width of the moveable valve element can ensure that the moveable valve element does not fit through the narrowed channel segment. In various examples, the moveable valve element can have a width from about 1 µm to about 100 µm.

The gap distance between the top of the moveable valve element and the microfluidic channel ceiling, as well as the gap between the bottom of the moveable valve element and the microfluidic channel floor, can affect the efficiency of the inertial pump and the ability of the inertial pump to work against a pressure head. In some examples, the height of the moveable valve element can be maximized to provide the best seal possible when the check valve is closed. However, a larger gap distance can be beneficial to ensure that the moveable valve element can move quickly between the open and closed valve positions. Thus, the gap distance can be selected to give good sealing when the valve is closed and also fast response time. The gap distance can also be influenced by the practicalities of manufacturing the inertial pump. In some examples, the moveable valve element can be manufactured by depositing a release layer on the microfluidic channel floor, forming the moveable valve element on the release layer, forming another release layer on the top of the moveable valve element, depositing the microfluidic channel ceiling, and then removing the release layer to free the moveable valve element from the floor and ceiling of the microfluidic channel. The gap distance in such examples can be controlled by the thickness of the release layers. In other examples, it can be desirable to have a more "leaky" pump that allows more backflow. In these examples, a larger gap distance can be used to tune the amount of backflow desired. In some examples, the gaps between the moveable valve element and the ceiling and floor of the microfluidic channel can have a gap height from about 0.05 µm to about 4 µm. In other examples, the moveable valve element can have a height that is from about 75% to about 99.9% the height of the microfluidic channel.

In other examples, the moveable valve element can be in the shape of a sphere. In some such examples, the microfluidic channel and elements of the check valve other than the spherical moveable valve element can be formed by photolithography. In certain examples, the microfluidic channel and check valve elements can be formed of an epoxy-based photoresist such as SU-8 or SU-8 2000 photoresist. The spherical moveable valve element can be a sphere made of the same material or a different material from the components of the check valve. In some cases, the material of the spherical moveable valve element can have a density close to the fluid flowing through the microfluidic channel, so that the spherical moveable valve element can follow fluid flowing through the microfluidic channel. In one example, the spherical moveable valve element can be placed in the microfluidic channel after forming the walls and floor of the microfluidic channel but before forming the ceiling of the microfluidic channel by placing a top layer over the microfluidic channel.

In certain examples, the check valve can be located from about 1 µm to about 100 µm away from the fluid actuator. In still further examples, the check valve can be located from about 1 µm to about 10 µm away from the fluid actuator.

In addition to the example check valve shown in FIGS. 1A-1D, a variety of other designs for check valves can be used. FIGS. 2-7 show various additional check valve designs.

Figure 2:
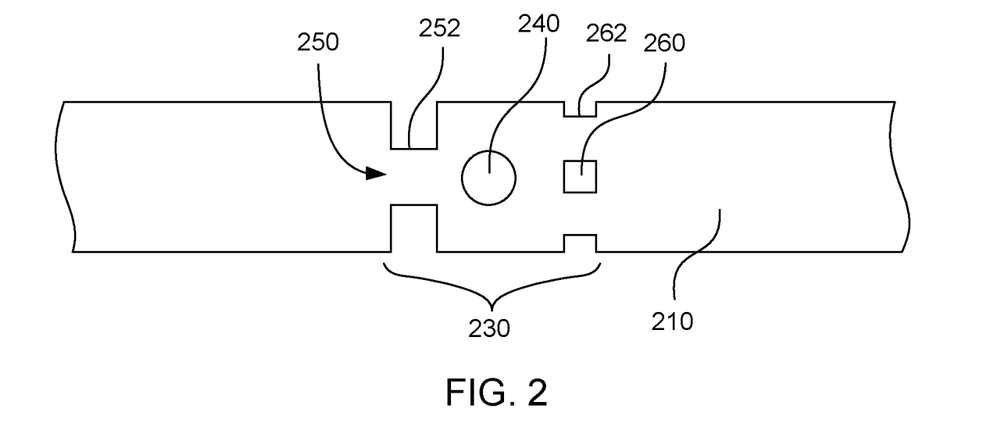
FIG. 2 is a top down schematic view of an example check valve in accordance with the present disclosure.

FIG. 2 shows an example microfluidic channel 210 with a check valve 230 including a narrowed channel segment 250 that is formed of two protrusions 252 of the channel walls. A blocking element 260 is located between two additional protrusions 262 from the channel walls. The moveable valve element 240 can be lodged in one gap between the blocking element and a protrusion, while fluid can flow through the gap on the other side of the blocking element.

Figure 3:
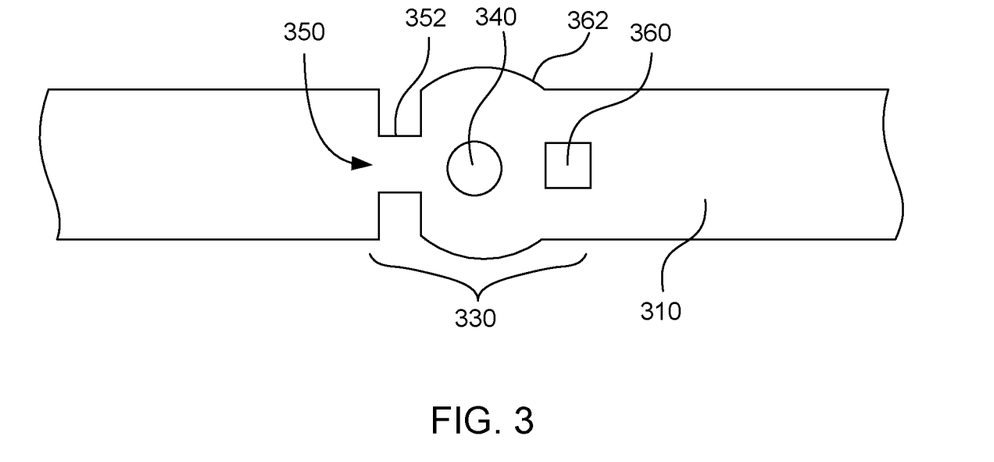
FIG. 3 is a top down schematic view of an example check valve in accordance with the present disclosure.

FIG. 3 shows an example microfluidic channel 310 with a check valve 330 that includes a narrowed channel segment 350 formed of two protrusions 352 from the channel walls. In this example, the blocking element 360 is placed proximate to curved channel wall segments 362. The curved channel wall segments can allow fluid to flow through the check valve more freely when the check valve is open. The gaps between the blocking element and the channel walls can be smaller than a width of the blocking element 340.

Figure 4:
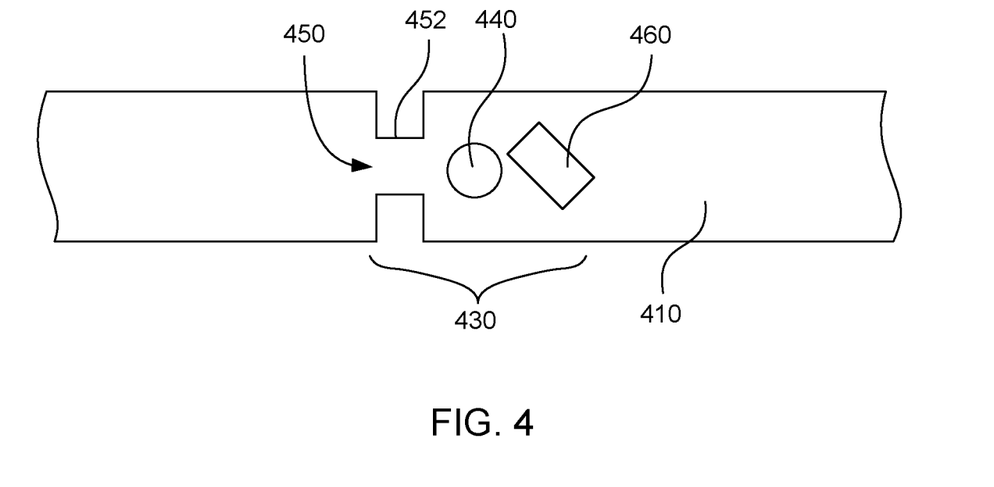
FIG. 4 is a top down schematic view of an example check valve in accordance with the present disclosure.

FIG. 4 shows an example microfluidic channel 410 with a check valve 430 that includes a narrowed channel segment 450 formed of two protrusions 452 from the channel walls. In this example, the blocking element 460 is a rotated rectangular pillar. The rotated shape of the pillar can encourage the moveable valve element 440 to lodge on one particular side of the pillar while fluid can flow past the other side of the blocking element when the valve is open.

Figure 5:
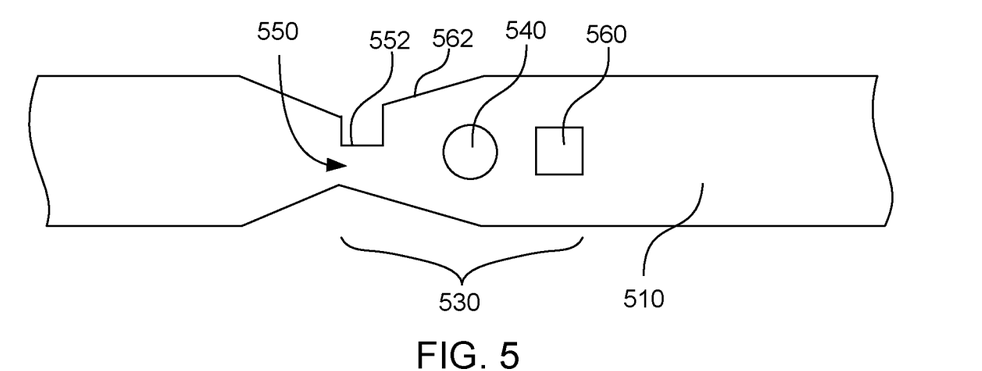
FIG. 5 is a top down schematic view of an example check valve in accordance with the present disclosure.

FIG. 5 shows an example microfluidic channel 510 with a check valve 530 that includes a narrowed channel segment 550 formed of converging wall segments 562 and a single protrusion 552. This example also has a blocking element 560 shaped as a square pillar and a cylindrical moveable valve element 540.

Figure 6:
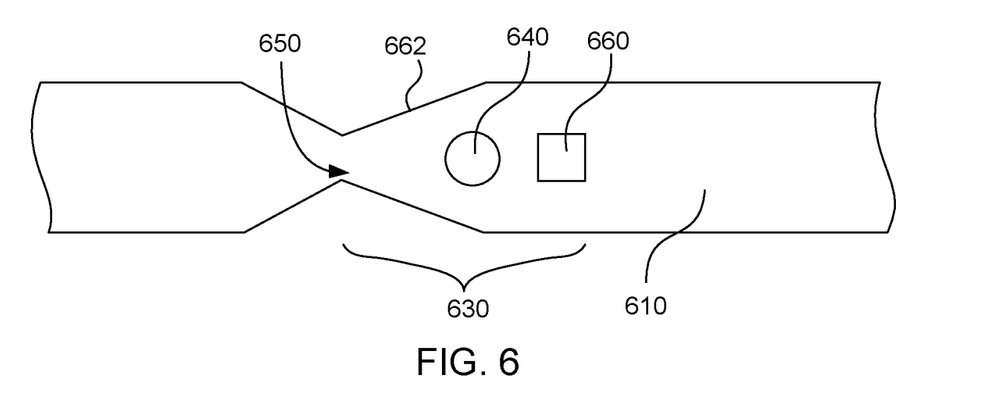
FIG. 6 is a top down schematic view of an example check valve in accordance with the present disclosure.

FIG. 6 shows an example microfluidic channel 610 with a check valve 630 that includes a narrowed channel segment 650 formed of converging wall segments 662 without any protrusions. This example also has a blocking element 660 shaped as a square pillar and a cylindrical moveable valve element 640.

Figure 7:
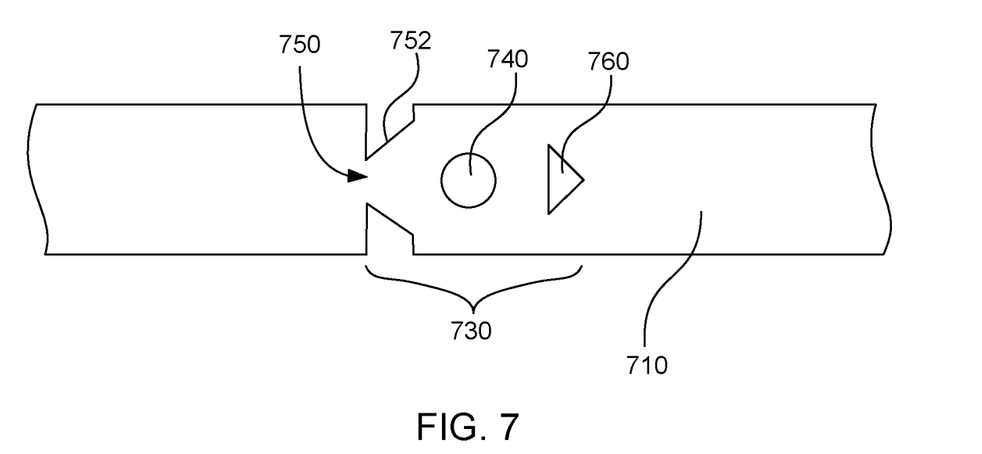
FIG. 7 is a top down schematic view of an example check valve in accordance with the present disclosure.

FIG. 7 shows an example microfluidic channel 710 with a check valve 730 that includes a narrowed channel segment 750 formed of two shaped protrusions 752 with converging slanted surfaces. The blocking element 760 is in the shape of a triangular block. The moveable valve 740 element is a cylinder. A variety of other designs can be devised for the presently described check valves.

In some examples, the inertial pumps described herein can be fabricated using photolithography. The microfluidic channel and the check valve structures can be formed from multiple layers, and the shaped of the microfluidic channel and check valve features can be formed by developing a photoresist material. In certain example, the layers can be formed from an epoxy-based photoresist. In one example, the layers can be formed from SU-8 or SU-8 2000 photoresist, which are epoxy-based negative photoresists. Specifically, SIJ-S and SU-8 200 are Bisphenol A Novolac epoxy-based photoresists that are available from various sources, including MECROCHEM® Corp. These materials can be exposed to UV light to become crosslinked, while portions that are unexposed remain soluble in a solvent and can be washed away to leave voids.

Figure 8:
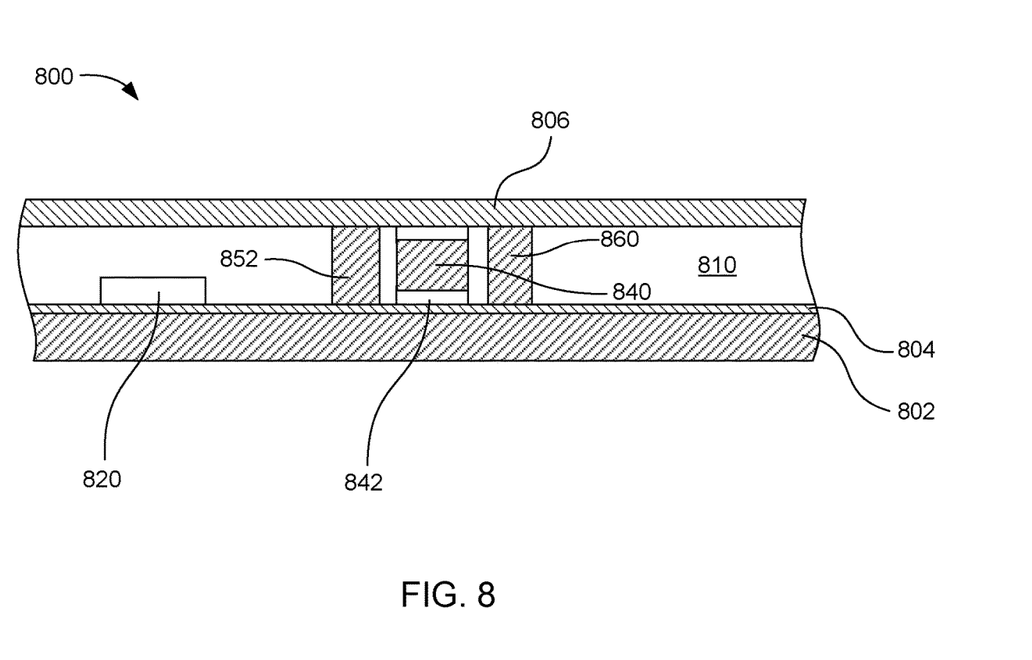
FIG. 8 is a side cross sectional view of an example inertial pump in accordance with the present disclosure.

FIG. 8 shows an example cross sectional view of an inertial pump 800 formed of multiple layers. A primer layer 804 is applied to a substrate 802. Then, a fluid actuator 820 can be deposited on the primer layer. In other examples, the fluid actuator can be formed on the substrate before applying the primer layer, and the primer can be removed from the top of the fluid actuator afterward. Alternatively, in some examples the primer layer can be applied over the fluid actuator and allowed to remain covering the fluid actuator. A microfluidic layer can then be deposited over the primer layer. The microfluidic layer can include the microfluidic channel walls that define a microfluidic channel 810, including protrusions 852 to form the narrowed channel segment, as well as the blocking element 860. In the location of the moveable valve element 840, a release layer 842 can first be deposited on the primer layer. The moveable valve element can then be formed over the release layer. A second release layer can be deposited on the top of the moveable valve element. A top layer 806 can then be applied over the microfluidic layer. After these layers are formed, the release layers can be removed to free the moveable valve element from the microfluidic channel ceiling and floor.

In another example, an inertial pump can be formed by depositing a film layer on a substrate, depositing a resistor on the film, then depositing a primer layer on the film. A lower moveable valve element release layer can then be deposited on a portion of the primer layer. Walls can be deposited on the primer layer to form a microfluidic channel. A moveable valve element can be deposited over the lower moveable valve element release layer within the microfluidic channel. A narrowed channel segment can be deposited upstream of the moveable valve element. A blocking element can be deposited downstream of the moveable valve element. An upper moveable valve element release layer can then be deposited on the moveable valve element. A top layer can be deposited over the walls, upper moveable valve element release layer, narrowed channel segment, and blocking element to form a ceiling of the microfluidic channel. Finally, the lower and upper moveable valve element release layers can be removed to allow the moveable valve element to move freely between the narrowed channel segment and the blocking element.

In some examples, the substrate can be formed of a silicon material. For example, the substrate can be formed of single crystalline silicon, polycrystalline silicon, gallium arsenide, glass, silica, ceramics or a semiconducting material. In a particular example, the substrate can have a thickness from about 50 μm to about 1200 μm.

In further examples, the primer layer can be a layer of a photoresist material, such as SU-8, with a thickness from about 2 μm to about 100 μm.

The microfluidic layer can be formed by exposing a layer of photoresist with a pattern of walls to define the covered fluid feed slots and microfluidic channels, and then washing away the unexposed photoresist. This layer can be formed by spin coating a liquid photoresist on the primer layer and then developing the layer, by laminating a dry photoresist film, or by a combination of both techniques. In some examples, the microfluidic layer can have a thickness from about 2 μm to 100 μm. The microfluidic channels can be formed having a width from about 2 μm to about 100 μm, from about 10 μm to about 50 μm, or from about 20 μm to about 30 μm.

In certain examples, the top layer can be formed by laminating a dry film photoresist over the microfluidic layer and exposing the dry film photoresist with a UV pattern to form the ceiling of the microfluidic channel. In some examples, the top layer can have a thickness from about 2 μm to about 200 μm.

Figure 9:
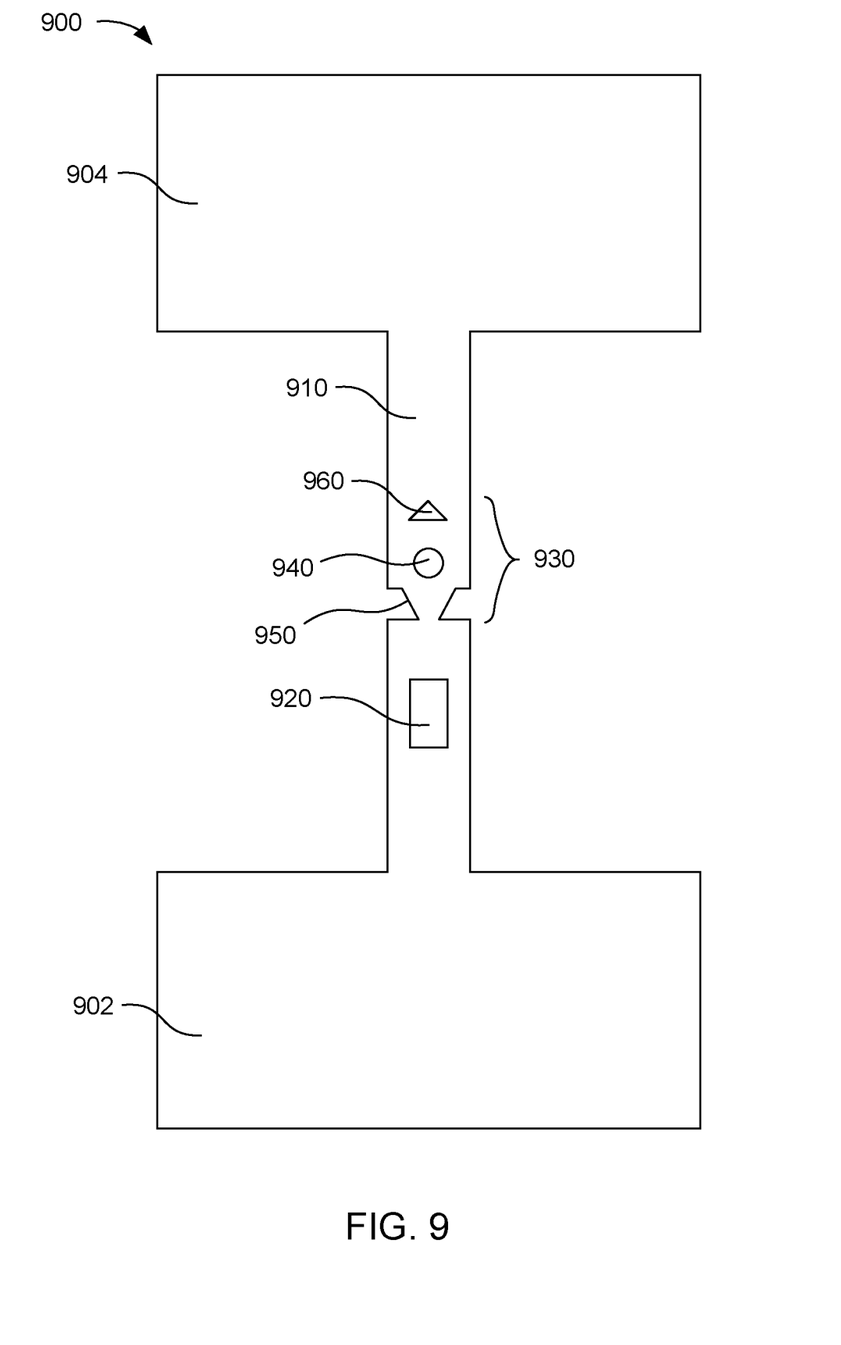
FIG. 9 is a top down schematic view of an example microfluidic device in accordance with the present disclosure.

The present technology also extends to microfluidic devices that incorporate the inertial pumps described above. FIG. 9 shows an example microfluidic device 900 that includes a first fluid reservoir 902, a second fluid reservoir 904, a microfluidic channel 910 connecting the fluid reservoirs, a fluid actuator 920 in the microfluidic channel, and a check valve 930 in the microfluidic channel. The check valve is made up of a narrowed channel segment 950, a blocking element 960, and a moveable valve element 940. In this example, the check valve is configured to allow flow from the first fluid reservoir toward the second fluid reservoir. Additionally, the check valve is located downstream from the fluid actuator in this example. With the check valve facing in this direction, the inertial pump made up of the fluid actuator and the check valve can pump fluid from the first fluid reservoir to the second fluid reservoir, even when the pressure in the second fluid reservoir is greater than the pressure in the first fluid reservoir.

Figure 10:
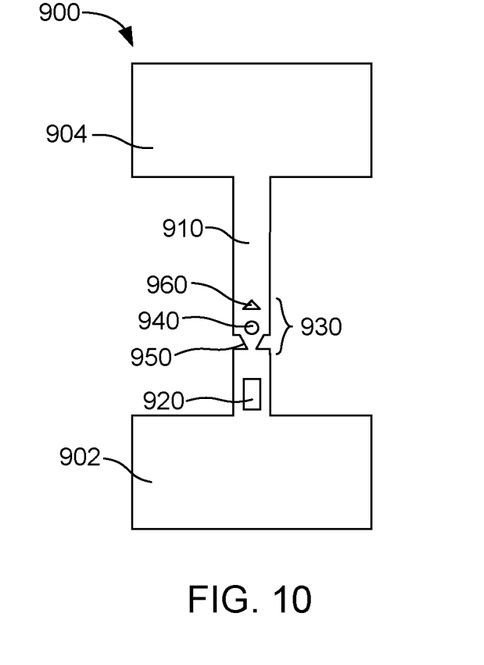
FIG. 10 is a top down schematic view of an example microfluidic device in accordance with the present disclosure.
Figure 11:
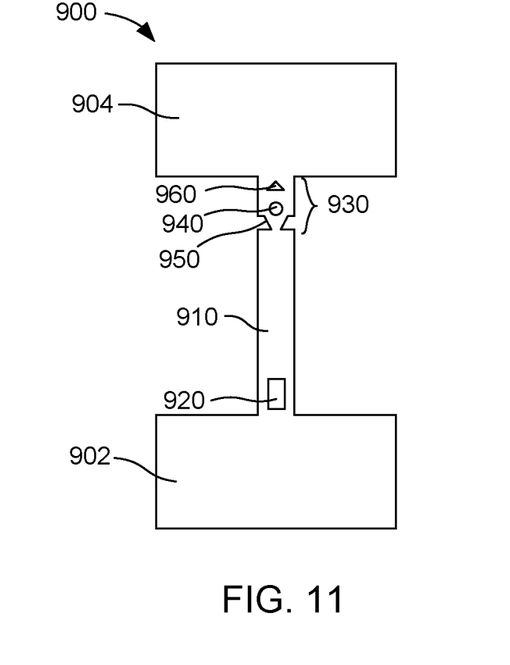
FIG. 11 is a top down schematic view of an example microfluidic device in accordance with the present disclosure.
Figure 12:
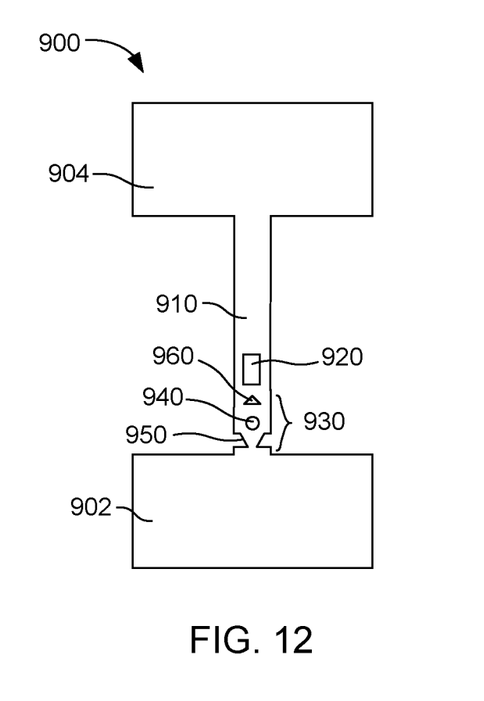
FIG. 12 is a top down schematic view of an example microfluidic device in accordance with the present disclosure.
Figure 13:
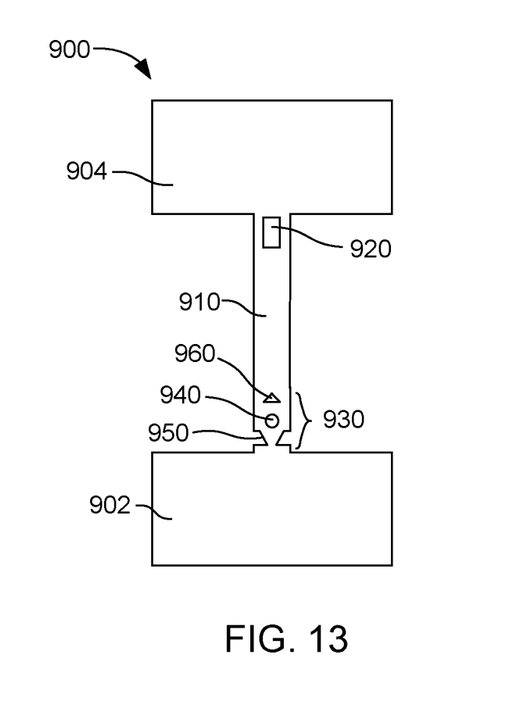
FIG. 13 is a top down schematic view of an example microfluidic device in accordance with the present disclosure.
Figure 14:
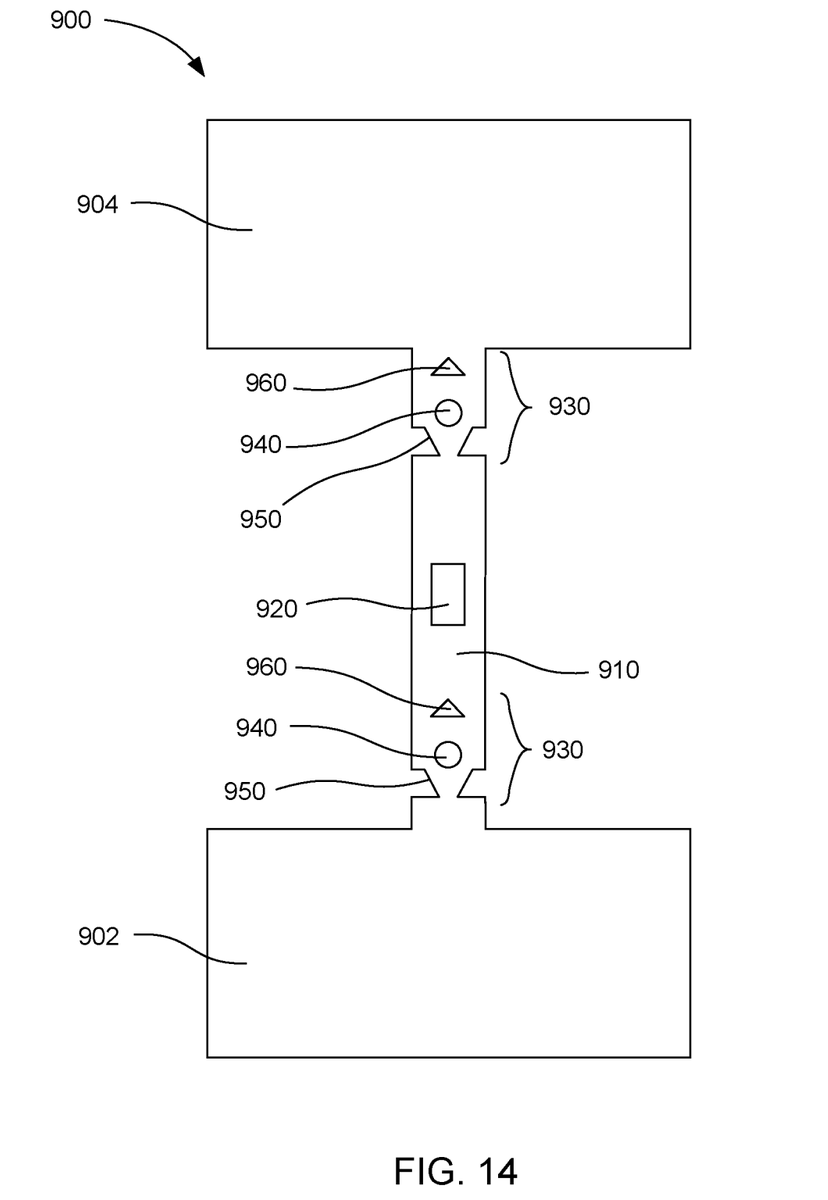
FIG. 14 is a top down schematic view of an example microfluidic device in accordance with the present disclosure.

FIGS. 10-13 show other example microfluidic devices 900 with the same components in different locations. Each of these examples is configured to pump fluid from the first fluid reservoir 902 to the second fluid reservoir 904. In FIG. 10, the fluid actuator 920 and check valve 930 are near the first fluid reservoir, with the check valve downstream of the fluid actuator. In FIG. 11, the fluid actuator is close to the first reservoir and the check valve is close to the second reservoir. In FIG. 12, the check valve and fluid actuator are close to the first reservoir, and the fluid actuator is downstream of the check valve. In FIG. 13, the check valve is near the first reservoir and the fluid actuator is near the second reservoir. FIG. 14 shows an example microfluidic device that includes two check valves. One check valve is upstream of the fluid actuator and the other check valve is downstream of the fluid actuator. All of these examples can produce fluid flow from the first reservoir into the second reservoir. Other designs can also be devised for the microfluidic devices described herein. Additionally, microfluidic devices can include more than two reservoirs, additional inertial pumps, other combinations of multiple fluid actuators and multiple check valves, and so on.

In further examples, the inertial pumps described herein can be used in microfluidic devices that mix multiple fluids together. Such devices can mix fluids for various purposes, such as dilution or reaction of the fluids. In one example, a microfluidic device can include a reservoir of a test fluid and a reservoir of a diluent fluid. Inertial pumps can be used to pump these two fluids into a common microfluidic channel or chamber to dilute the test fluid. In another example, a microfluidic device can include two or more reservoirs of reactants. Inertial pumps can be used to mix the reactants together in a reactor to perform a chemical reaction.

In various examples, fluids that can be pumped by the inertial pumps can include water, aqueous fluids such as aqueous solutions and dispersions, alcohols, silicon oils, organic liquids, and many others. In certain examples, test fluids can include biological fluids or aqueous solutions of biological molecules. In further examples, diluent fluids can include water, alcohols, or aqueous solutions such as saline solution. Reactant fluids can include any liquid reactants, solutions of dissolved reactants, dispersions of solid reactants, and so on. In some examples, the fluid can include dispersed solid particles that have a particle size small enough to fit through the microfluidic channels and check valves used.

Figure 15:
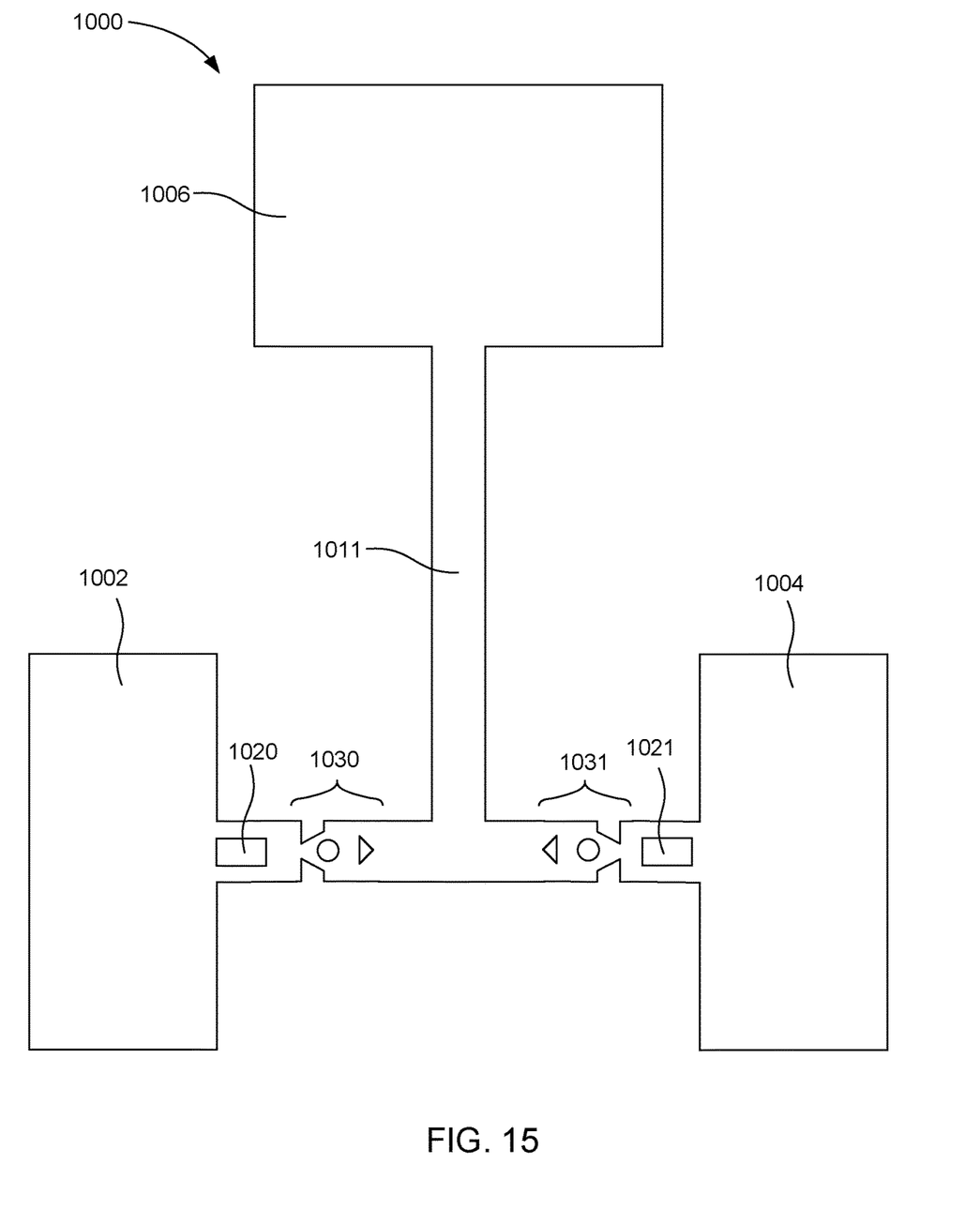
FIG. 15 is a top down schematic view of an example microfluidic device in accordance with the present disclosure.

FIG. 15 shows an example microfluidic device 1000 that includes a microfluidic mixing channel 1011, a first fluid reservoir 1002, a second fluid reservoir 1004, and a reactor 1006. A first inertial pump is made up of a first fluid actuator 1020 and a first check valve 1030. The first inertial pump is connected between the first reservoir and the microfluidic mixing channel. A second inertial pump is made up of a second fluid actuator 1021 and a second check valve 1031. The second inertial pump is connected between the second reservoir and the microfluidic mixing channel.

The microfluidic device shown in FIG. 15 can be used to mix reactants or dilute fluids. In one example, the first and second reactors can contain different reactants. In another example, the first reservoir can contain a fluid to be diluted, and the second reservoir can contain a diluent fluid. One advantage provided by the inertial pumps in this device is the check valves can substantially prevent mixing the two different fluids in the reservoirs. For example, it can be undesirable to have two reactants mix within either the first or second fluid reservoir. The check valves in the first and/or second inertial pumps can prevent the reactant from the first reservoir from entering the second reservoir, and vice versa.

In a particular example, a microfluidic device as described herein can be used for DNA testing. In this example, a first fluid reservoir can contain biological cells of interest mixed with a lysis buffer. A first inertial pump as described herein can pump the first fluid from the first fluid reservoir into a reaction chamber. A second fluid reservoir can include a washing buffer. After the biological cells and lysis buffer have reacted in the reaction chamber, the washing buffer can be pumped by a second inertial pump into the reaction chamber to wash the reaction chamber. The check valves in the first and second inertial pumps can prevent the biological cells and lysis buffer from entering into the second fluid reservoir and also prevent the washing buffer from entering into the first fluid reservoir.

In further examples, three or more reservoirs can be connected to microfluidic channels that meet at a single intersection. Each reservoir can have an associated inertial pump with a check valve in each microfluidic channel. Such a device can be used to mix multiple different materials together or to pump multiple different materials sequentially, without mixing the materials in any of the reservoirs.

Another advantage provided by the inertial pumps is the ability to control a mixing ratio of the fluids in the first and second reservoirs. In some examples, the flow rates of the fluids from the reservoirs can be controlled by controlling the firing frequency of the first and second fluid actuators. For example, if the first fluid actuator is fired with twice the frequency of the second fluid actuator, then the flow rate of fluid from the first reservoir can be about twice the flow rate of fluid from the second reservoir. The ratio of flow rates can be finely controlled be adjusting the relative firing rates of the fluid actuators. Thus, in some examples reactions requiring specific ratios of several reactants can be performed by the microfluidic device. In other examples, the microfluidic device can provide a specific dilution of a fluid by control the flow rate of the fluid and the diluent fluid from the respective reservoirs. These microfluidic devices can also be useful for adding reactants into a reactor in a particular sequence, as the inertial pumps associated with each reservoir can be activated in any desired sequence.

In a further example, a microfluidic device can be fabricated with multiple parallel inertial pumps leading from the first and/or second reservoirs to the mixing channel. Including additional inertial pumps can increase the range of ratios of the flow rates that can be achieved. Additional inertial pumps can also improve the precision of control over the flowrates, because the firing rate of each inertial pump can be separately controlled to precisely control the flow rates.

It is to be understood that this disclosure is not limited to the particular process steps and materials disclosed herein because such process steps and materials may vary somewhat. It is also to be understood that the terminology used herein is used for the purpose of describing particular examples only. The terms are not intended to be limiting because the scope of the present disclosure is intended to be limited only by the appended claims and equivalents thereof.

It is noted that, as used in this specification and the appended claims, the singular forms "a," "an," and "the" include plural referents unless the context clearly dictates otherwise.

As used herein, the term "substantial" or "substantially" when used in reference to a quantity or amount of a material, or a specific characteristic thereof, refers to an amount that is sufficient to provide an effect that the material or characteristic was intended to provide. The exact degree of deviation allowable may in some cases depend on the specific context.

As used herein, the term "about" is used to provide flexibility to a numerical range endpoint by providing that a given value may be "a little above" or "a little below" the endpoint. The degree of flexibility of this term can be dictated by the particular variable and determined based on the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

EXAMPLES

The following illustrates an example of the present disclosure. However, it is to be understood that the following are only illustrative of the application of the principles of the present disclosure. Numerous modifications and alternative compositions, methods, and systems may be devised without departing from the spirit and scope of the present disclosure. The appended claims are intended to cover such modifications and arrangements.

Example 1—Microfluidic Check Valve Simulation

Figure 16:
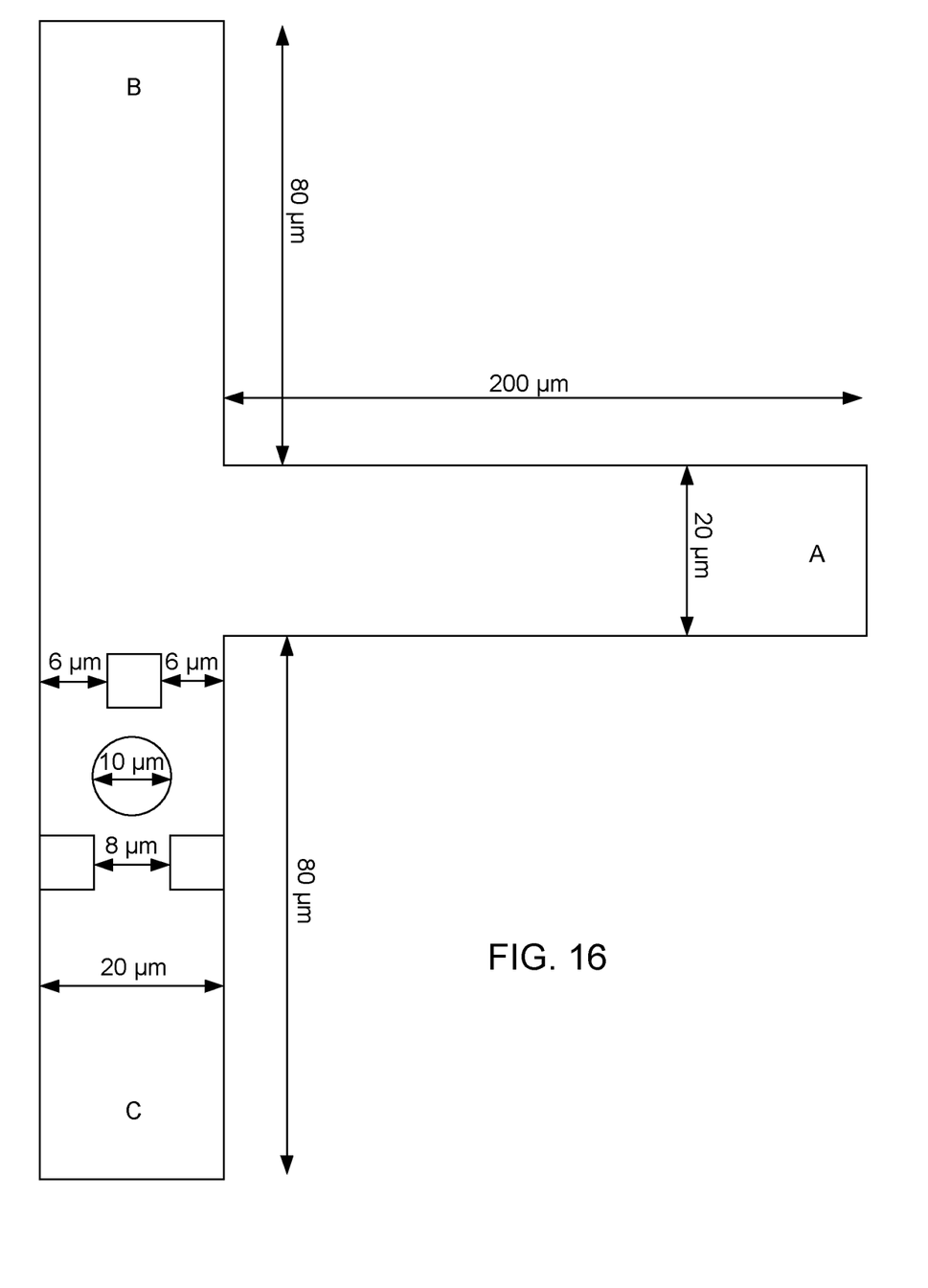
FIG. 16 is a top down schematic view of a geometry used for a fluid dynamic simulation of a check valve in accordance with the present disclosure.

A computer simulation was performed using the geometry of an example microfluidic system shown in FIG. 16. This figure shows the dimensions of the geometry in a top down view. The height of the channels was set to 20 μm and the height of the cylindrical moveable valve element was 15 μm. A fluid dynamic simulation was performed to simulate the flow of water through these microfluidic channels with flow coming from channel A. The simulation showed that the cylindrical moveable valve element was moved by the flowing fluid and contacted the narrowed channel segment after about 10 μs. Once the valve was closed, approximately three times as much fluid flowed into channel B as flowed into channel C.

The direction of flow was then changed so that the flow originated from both channels B and C. The cylindrical moveable valve element moved to one side of the blocking element, and fluid flowed around the other side of the blocking element and into channel A. The volumetric flow rate from channel C into channel A was found to be less than the volumetric flow rate from channel B into channel A, because channel B did not have a check valve interfering with the flow. The simulations indicate that the check valve can effectively reduce fluid flow through the check valve when in a closed position while allowing fluid to flow when in an open position. The check valve also has a fast response time of 10 μs.

While the present technology has been described with reference to certain examples, various modifications, changes, omissions, and substitutions can be made without departing from the spirit of the disclosure. It is intended, therefore, that the disclosure be limited only by the scope of the following claims.

What is claimed is:

1. An inertial pump, comprising:
   a microfluidic channel;
   a fluid actuator located in the microfluidic channel; and
   a check valve located in the microfluidic channel, the check valve comprising:
   a moveable valve element,
   a narrowed channel segment located upstream of the moveable valve element, the narrowed channel segment having a width less than a width of the moveable valve element such that the moveable valve element blocks fluid flow through the check valve when the moveable valve element is positioned in the narrowed channel segment, and
   a blocking element formed in the microfluidic channel downstream of the moveable valve element and configured such that the blocking element constrains the moveable valve element within the check valve while also allowing fluid flow when the moveable valve element is positioned against the blocking element.

2. The inertial pump of claim 1, wherein the fluid actuator is a resistor configured to generate vapor bubbles to displace fluid in the microfluidic channel.

3. The inertial pump of claim 1, wherein the microfluidic channel and the check valve are fabricated by photolithography.

4. The inertial pump of claim 1, wherein a distance between the blocking element and the narrowed channel segment is from 1.1 to 5 times the width of the moveable valve element.

5. The inertial pump of claim 1, wherein the moveable valve element is in the form of a cylinder or a hexagonal block.

6. The inertial pump of claim 1, further comprising gaps between the moveable valve element and a ceiling and floor of the microfluidic channel, wherein the gaps have a height from about 0.05 µm to about 4 µm.

7. The inertial pump of claim 1, wherein the check valve is located from 1 µm to 100 µm away from the fluid actuator.

8. The inertial pump of claim 1, wherein the check valve is located downstream of the fluid actuator.

9. The inertial pump of claim 8, further comprising a second check valve located upstream of the fluid actuator.

10. A microfluidic device, comprising:
    a fluid reservoir;
    a microfluidic channel in communication with the fluid reservoir;
    a fluid actuator located in the microfluidic channel; and
    a check valve located in the microfluidic channel, the check valve comprising:
    a moveable valve element,
    a narrowed channel segment located upstream of the moveable valve element, the narrowed channel segment having a width less than a width of the moveable valve element such that the moveable valve element blocks fluid flow through the check valve when the moveable valve element is positioned in the narrowed channel segment, and
    a blocking element formed in the microfluidic channel downstream of the moveable valve element and configured such that the blocking element constrains the moveable valve element within the check valve while also allowing fluid flow when the moveable valve element is positioned against the blocking element.

11. The microfluidic device of claim 10, wherein the check valve is configured to allow fluid flow away from the fluid reservoir.

12. The microfluidic device of claim 11, wherein the fluid reservoir is a first fluid reservoir, wherein the microfluidic device further comprises a second fluid reservoir in communication with the microfluidic channel, wherein the check valve is located along the microfluidic channel between the first fluid reservoir and the second fluid reservoir, and wherein the second fluid reservoir has a higher pressure than the first fluid reservoir.

13. A microfluidic device, comprising
    a microfluidic mixing channel;
    a first fluid reservoir;
    a first inertial pump fluidly connected between the first fluid reservoir and the microfluidic mixing channel to pump a first fluid from the first fluid reservoir into the microfluidic mixing channel;
    a second fluid reservoir; and
    a second inertial pump fluidly connected between the second fluid reservoir and the microfluidic mixing channel to pump a second fluid from the second fluid reservoir into the microfluidic mixing channel;
    wherein one or both of the first and second inertial pumps comprise:
    a microfluidic channel,
    a fluid actuator located in the microfluidic channel, and
    a check valve located in the microfluidic channel, the check valve comprising:
    a moveable valve element;
    a narrowed channel segment located upstream of the moveable valve element, the narrowed channel segment having a width less than a width of the moveable valve element such that the moveable valve element blocks fluid flow through the check valve when the moveable valve element is positioned in the narrowed channel segment; and
    a blocking element formed in the microfluidic channel downstream of the moveable valve element and configured such that the blocking element constrains the moveable valve element within the check valve while also allowing fluid flow when the moveable valve element is positioned against the blocking element.

14. The microfluidic device of claim 13, further comprising one or more additional first inertial pump fluidly connected between the first fluid reservoir and the microfluidic mixing channel, and one or more additional second inertial pump fluidly connected between the second fluid reservoir and the microfluidic mixing channel.

15. The microfluidic device of claim 13, wherein the microfluidic mixing channel leads to a reactor.

* * * * *